US00PP20106P2

(12) United States Plant Patent
Bradford

(10) Patent No.: US PP20,106 P2
(45) Date of Patent: Jun. 16, 2009

(54) INTERSPECIFIC TREE NAMED 'PLUMSWEET XII'

(50) Latin Name: ***Prunus* sp.**
Varietal Denomination: Plumsweet XII

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 29 days.

(21) Appl. No.: 11/984,888

(22) Filed: Nov. 26, 2007

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP13,476 P2 1/2003 Bradford
PP14,220 P2 10/2003 Bradford

*Primary Examiner*—Kent L Bell

(57) ABSTRACT

The present invention relates to an interspecific tree and more particularly to a new and distinct variety broadly characterized by a medium size, moderately vigorous, hardy, and medium productive tree. Being self-unfruitful, the present variety requires cross pollination from an apricot, interspecific, or plum that blooms during the mid season. The fruit matures under the ecological conditions described during early July, with first picking on Jul. 7, 2007. The fruit is uniformly medium in size, mostly red with greenish yellow freckling in skin color, clingstone in type, oblate in shape, red in flesh color, very firm and crisp in texture, and outstanding in flavor.

1 Drawing Sheet

Botanical classification: *Prunus* sp.
Varietal denomination: 'PLUMSWEET XII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Plumsweet XII'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one such house containing an unpatented red plum, code named 19P442, was crossed by me in this manner. To pollinate this red plum, I selected bouquets from several sources of apricot and interspecific plum-apricot hybrid trees without keeping specific written details. Upon reaching maturity the fruit from this red plum tree was harvested and the seeds were removed, cracked, stratified and germinated as a group with the label "H5". They were grown as seedlings on their own root in my greenhouse and upon reaching dormancy transplanted to a cultivated area of my experimental orchard located near Le Grand, Calif. in Merced County (San Joaquin Valley). During the summer of 2004 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'YUMMY®rosa' (U.S. Plant Pat. No. 13,476) plum by being self-unfruitful and by producing fruit that is medium in size, that is clingstone in type, and that is somewhat oblate in shape, but is distinguished therefrom by having a flower that produces less pollen and by producing fruit that is firmer in texture, that is entirely red in flesh color, that has abundant greenish yellow freckling, that is somewhat sweeter in flavor, and that matures about seventeen days later.

SUMMARY OF VARIETY

The present interspecific variety is characterized by a medium size, moderately vigorous, hardy, and medium productive tree. Being self-unfruitful, the present variety requires cross pollination from an apricot, interspecific, or plum that blooms during the mid season. The fruit matures under the ecological conditions described during early July, with first picking on Jul. 7, 2007. The fruit is uniformly medium in size, mostly red with greenish yellow freckling in skin color, clingstone in type, oblate in shape, red in flesh color, very firm and crisp in texture, and outstanding in flavor.

DRAWING

The accompanying photograph consists of four whole fruits positioned to display the characteristics of the skin color and form, two half fruits divided to reveal the flesh and stone, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Jul. 17, 2007, on the original tree during its sixth growing season. The flower and bud descriptions were developed during the previous blooming season. All major color code designations are by reference to the Inter-Society Color Council, National Bureau of Standards. Common color names are also used occasionally.

Parentage

Seed Parent: 19P442 plum (unpatented).
Pollen Parent: Unknown.

Tree

Size: Medium, reaching and maintaining a height of 10' [3.05 m.] and a spread of 6' [1.83 m.] after six growing seasons utilizing typical dormant pruning.

Vigor: Moderately vigorous, responding typically to irrigation and fertilization. The variety grows about 3' [0.914 m.] of surplus top-growth during the spring and summer. The plant should be grown on a standard commercial rootstock for production purposes.

Growth: Upright and dense.

Form: Central leader type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Medium productive, thinning sometimes necessary.

Fertility: Self-unfruitful, requiring cross pollination by a suitable mid seasonal blooming apricot, interspecific, or plum, such as 'September YUMMY®' (U.S. Plant Pat. No. 14,220).

Bearing: Uncertain bearer, dependent upon suitable weather during the blooming season.

Trunk:

- *Size.*—Medium to small, reaching a maximum diameter of 3" [76 mm.] after the sixth growing season.
- *Texture.*—Shaggy.
- *Bark color.*—A Grayish brown [61. gy.Br] and Dark grayish brown [62. d.gy.Br] variegation with Light yellowish brown [76. l.yBr] crevices present.
- *Lenticels.*—Approximate Number Per Square Inch: 8. Color: Light grayish yellowish brown [79. l.gy.yBr]. Average Size: ¼" [6.4 mm.]. Shape: Eye-shaped, elongated.

Branches:

- *Size.*—Diameter of limb is 1" [25.4 mm.] measured 12" from central leader.
- *Texture.*—Smooth on first and second year wood, increasing roughness with age.
- *Color.*—1st Year Wood Topside: Light brown [57. l.Br]. 1st Year Wood Underside: Brilliant yellow green [116. brill.YG]. Older Wood: Dark grayish brown [62. d.gy.Br].
- *Lenticels.*—Number Per Square Inch: More than 60 on second year wood. Color: Moderate orange yellow [71. m.OY]. Average Size: 1/32" [0.8 mm.]. Shape: Elongated, rectangular.

Leaves:

- *Size.*—Medium. Average Length: 3 11/16" [94 mm.]. Average Width: 2⅛" [54 mm.].
- *Arrangement.*—Alternate.
- *Thickness.*—Medium.
- *Form.*—Elliptical.
- *Apex.*—Mucronate to somewhat acuminate.
- *Base.*—Mostly acute with an average base angle of 75 degrees, some obtuse.
- *Surface.*—Smooth.
- *Color.*—Dorsal Surface: Moderate olive green [125. m.O1G]. Ventral Surface: Moderate olive green [125. m.OlG].
- *Margin.*—Finely serrate.
- *Venation.*—Pinnately net veined.
- *Petiole.*—Average Length: 9/16" [14.3 mm.]. Average Thickness: 1/32" [0.8 mm.]. Color: Light yellow green [119. l.YG].
- *Stipules.*—Number: 2 per leaf, up to 6 per growing tip. Average Length: ¼" [6.4 mm.]. Color: Very yellow green [115. v.YG] becoming Moderate reddish brown [43. m.rBr] with age.
- *Glands.*—Number: Mostly 2 per leaf. Position: Alternately positioned at the intersection of the petiole and the leaf blade. Size: Small. Form: Globose. Color: Brilliant yellow green [116. brill.YG] becoming Deep reddish brown [41. deep rBr] in the center with age. Leaf buds: Pointed, medium.

Flower buds:

- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Tip color.*—White [263. White].

Flowers: Perfect, complete, perigynous, usually a single pistil, typically thirty or more stamens, five sepals and petal locations alternately positioned.

- *Average flower diameter.*—1 1/16" [27.0 mm.].
- *Number of petals.*—Five, no double blossoms observed.
- *Petal shape.*—Oval.
- *Petal margin.*—Entire, wavy with some notches.
- *Average petal diameter.*—7/16" [11 mm.].
- *Average petal length.*—9/16" [14.3 mm.].
- *Petal apex.*—Rounded.
- *Petal base.*—Slightly acute, with an average base angle of 80 degrees.
- *Petal color.*—White [263. White] on both sides.
- *Anther color.*—Light greenish yellow [101. l.gY].
- *Stigma color.*—Light greenish yellow [101. l.gY].
- *Sepal color.*—Brilliant yellow green [116. brill.YG].
- *Sepal length.*—5/32" [4.0 mm.].
- *Sepal width.*—5/32" [4.0 mm.].
- *Sepal apex.*—Rounded to elliptical to match the width and length.
- *Sepal margin.*—Fairly smooth, with slight serrations present.
- *Average pistil length.*—⅝" [15.9 mm.].
- *Average stamen length.*—½" [12.7 mm.].
- *Fragrance.*—Moderate.

*Pollen production.*—Slight.
*Blooming period.*—Medium, two before 'Santa Rosa' plum (unpatented).
*Onset of bloom.*—One percent on Feb. 26, 2007.
*Date of full bloom.*—Mar. 6, 2007.
*Duration of bloom.*—One to two weeks, dependent on ambient temperature.
*Bloom density.*—Moderate.
*Number per cluster.*—2 to 7, average 4.

FRUIT

Maturity when described: Firm ripe, Jul. 17, 2007.
Date of first picking: Jul. 7, 2007.
Date of last picking: Jul. 17, 2007.
Size: Uniform, Medium.
*Average diameter axially.*—2 1/16" [52.4 mm.].
*Average diameter across cheek plane.*—2 7/16" [61.9 mm.].
*Average diameter across suture plane.*—2 1/4" [57.2 mm.].
*Typical weight.*—4.4 ounces [125 grams].
Form: Uniform, globose to oblate, symmetrical.
*Longitudinal section form.*—Round to ovate.
*Transverse section through diameter.*—Round to slightly elliptical.
Suture: A distinct line located in a very shallow groove extending from the base to just beyond the apex.
Ventral surface: Rounded, slightly lipped toward the base.
Lips: Equal.
Cavity: Flaring, rounded, suture showing on one side.
*Depth.*—1/4" 46.4 mm.].
*Breadth.*—3/4" [19.1 mm.].
Base: Truncate, slightly cordate if viewed parallel to the suture.
Apex: Truncate.
Pistil point: An inconspicuous dot.
Stem: Medium.
*Average length.*—3/8" [9.5 mm.].
*Average width.*—5/64" [2.0 mm.].
Skin:
*Thickness.*—Medium.
*Surface.*—Smooth.
*Tenacity.*—Tenacious to the flesh.
*Astringency.*—Moderate.
*Tendency to crack.*—Slight.
*Color.*—Very dark red [17. v.d.R] with Deep greenish yellow [100. deep gY] mottling and Moderate greenish yellow [102. m.gY] freckling throughout.
*Bloom.*—Abundant.
Flesh:
*Color.*—Dark red [16. d.R] toward the stone, Very deep red [14. v.deep R] toward the skin.
*Surface of pit cavity.*—Covered with Deep red [13. deep R] fibers when twisted away from the stone.
*Amygdalin.*—Moderate.
*Juice.*—Abundant, rich.
*Texture.*—Firm, crisp.
*Fibers.*—Abundant, fine, tender.
*Ripens.*—Slightly earlier toward the apex.
*Flavor.*—A tasty blend of acid and sugar, typically 20 brix.
*Aroma.*—Moderate.
*Eating quality.*—Outstanding.

STONE

Type: Clingstone.
Form: Oval.
Hilum: Narrow.
Base: Straight.
Apex: Acuminate, with a sharp 1/8" [3.2 mm.] tip.
Sides: Equal.
Surface: Rough throughout with one deep groove from base to apex on each side of the dorsal fin.
External color of stone: Strong yellowish brown [74. s.yBr].
Pit wall color when cracked: Light yellowish brown [76. l.yBr].
Cavity surface color: Dark orange yellow [72. d.OY].
Average pit wall thickness: 1/32" [0.8 mm.].
Average width: 3/4" [19.1 mm.].
Average length: 9/16" [14.3 mm.].
Average breadth: 5/16" [7.9 mm.].
Tendency to split: None observed.
Kernel:
*Form.*—Oval.
*Skin color.*—Pale yellow [89. p.Y] when first removed.
*Pellicle color.*—Moderate yellowish brown [77. m.yBr].
*Vein color.*—Strong yellowish brown [74. s.yBr].
*Taste.*—Bitter.
*Viable.*—Yes.
*Average width.*—3/8" [9.5 mm.].
*Average length.*—9/16" [14.3 mm.].
*Amygdalin.*—Moderate.

Use

Market: Fresh market and long distance shipping.
Keeping guality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'YUMMY®rosa' (U.S. Plant Pat. No. 13,476) plum by being self-unfruitful and by producing fruit that is medium in size, that is clingstone in type, and that is somewhat oblate in shape, but is distinguished therefrom by having a flower that produces less pollen and by producing fruit that is firmer in texture, that is entirely red in flesh color, that has abundant greenish yellow freckling, that is somewhat sweeter in flavor, and that matures about seventeen days later.

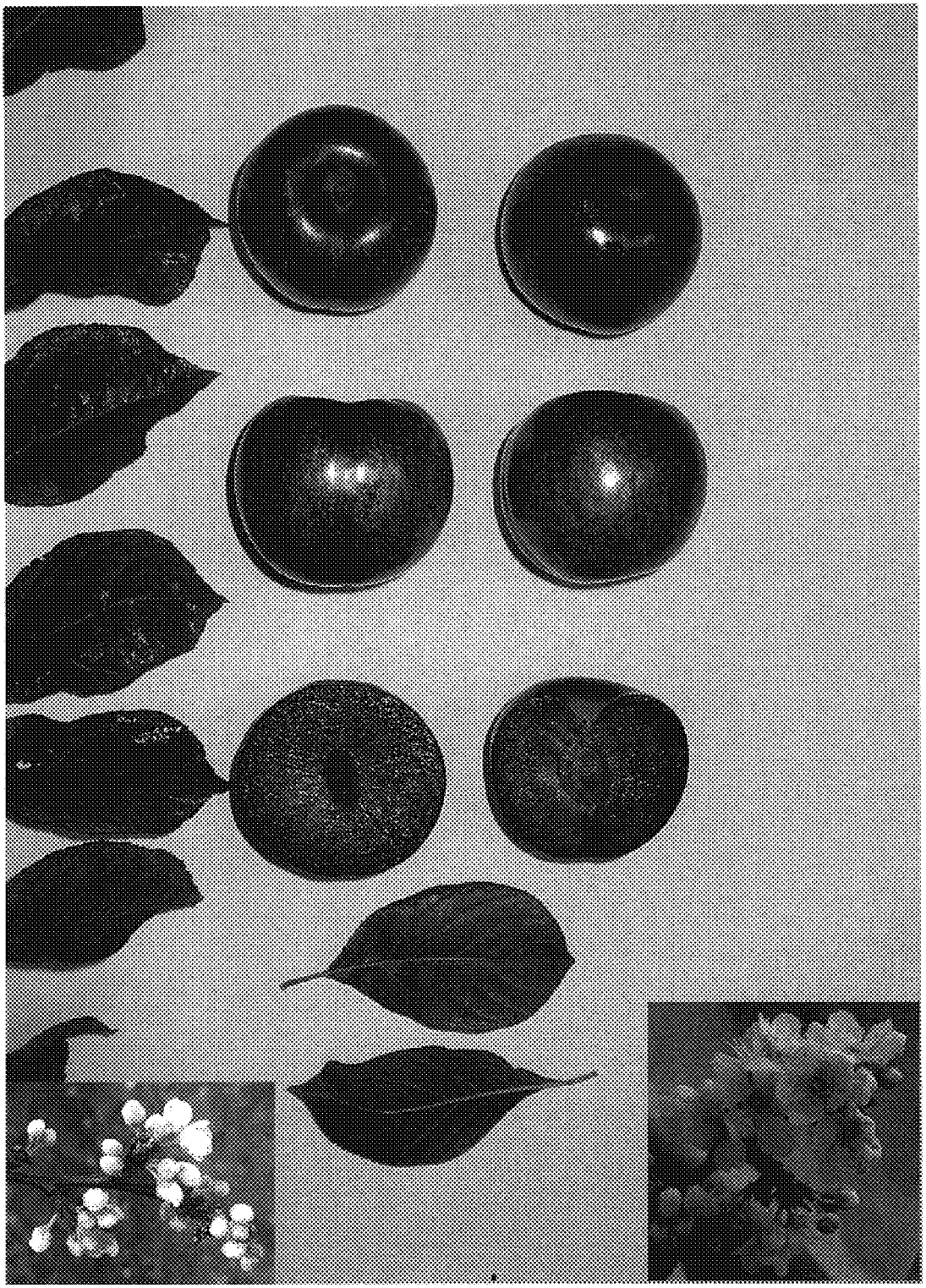

* * * * *